United States Patent [19]

Schuss et al.

[11] Patent Number: 4,753,595
[45] Date of Patent: Jun. 28, 1988

[54] DENTAL HANDPIECE

[75] Inventors: Werner Schuss, Heppenheim; Walter Weber, Bensheim; Siegfried Goisser, Einhausen, all of Fed. Rep. of Germany

[73] Assignee: Siemens Aktiengesellschaft, Berlin and Munich, Fed. Rep. of Germany

[21] Appl. No.: 898,997

[22] Filed: Aug. 22, 1986

[30] Foreign Application Priority Data

Aug. 26, 1985 [DE] Fed. Rep. of Germany ....... 3530461

[51] Int. Cl.$^4$ ............................................. A61C 1/12
[52] U.S. Cl. ....................................... 433/133; 433/29
[58] Field of Search ................. 433/29, 84, 85, 126, 433/128, 133

[56] References Cited

U.S. PATENT DOCUMENTS

| | | | |
|---|---|---|---|
| 3,893,242 | 7/1975 | Lieb et al. | 433/29 |
| 4,217,101 | 8/1980 | Loge | 433/126 |
| 4,235,595 | 11/1980 | Arnegger | 433/131 |
| 4,255,143 | 3/1981 | Schuss et al. | 433/126 |
| 4,332,562 | 6/1982 | Schuss et al. | 433/126 |
| 4,348,180 | 9/1982 | Schuss | 433/126 |
| 4,398,885 | 8/1983 | Loge et al. | 433/29 |

FOREIGN PATENT DOCUMENTS

| | | |
|---|---|---|
| 0029860 | 6/1981 | European Pat. Off. . |
| 0029862 | 3/1984 | European Pat. Off. . |
| 2756011 | 12/1978 | Fed. Rep. of Germany . |

Primary Examiner—Robert Peshock
Assistant Examiner—Adriene J. Lepiane
Attorney, Agent, or Firm—Hill, Van Santen, Steadman & Simpson

[57] ABSTRACT

A dental handpiece, which has a gripping part connectable to a supply hose and a head part with a head housing which is removably held at the free end of the gripping part, characterized by the gripping part having at least one light conductor with an end located adjacent to the connection between the two parts to project light therefrom and having an inclined free end surface engaging an inclined oblique surface of the head part with the surfaces extending so that the lower end thereof merges with the head housing. A lower portion of the end surface is formed by a carrier part which accepts the ends of the light conductors to project light into the area of the tool held by the housing of the head part.

17 Claims, 2 Drawing Sheets

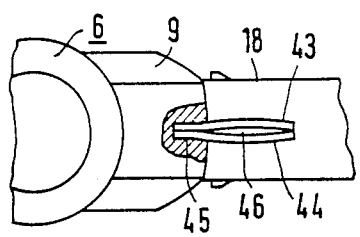
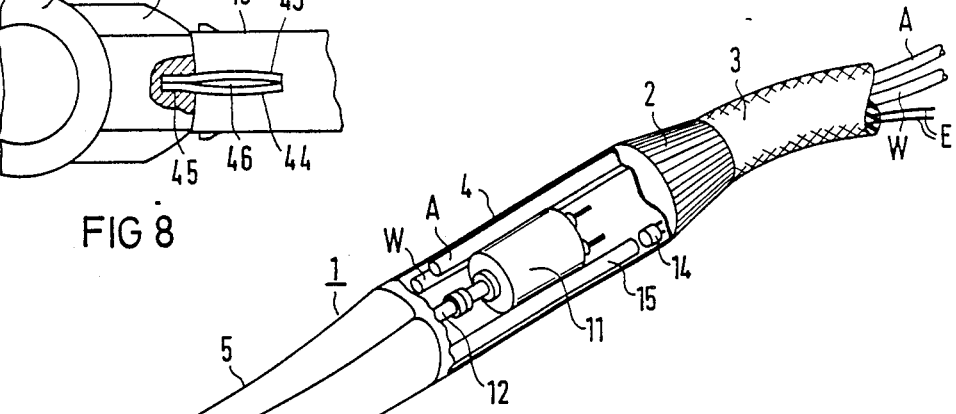
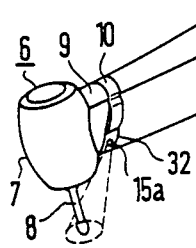
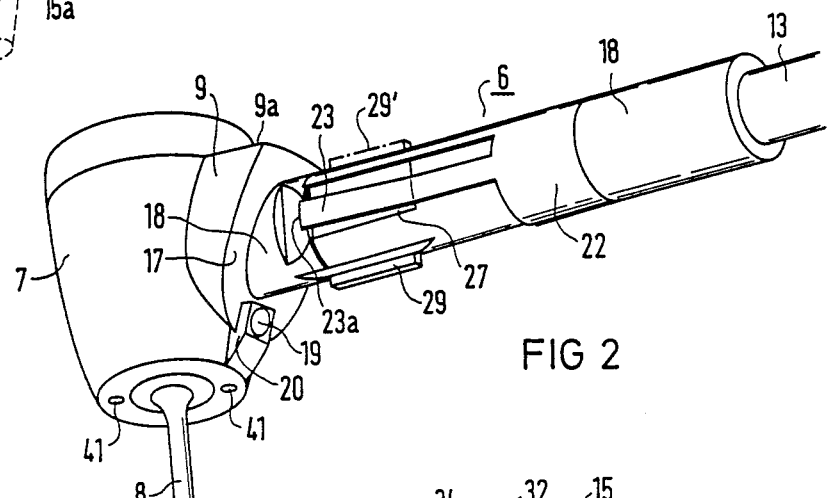
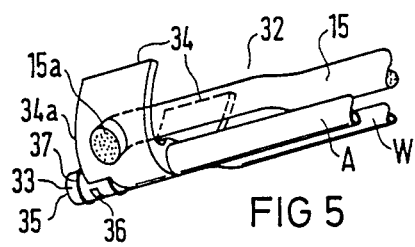

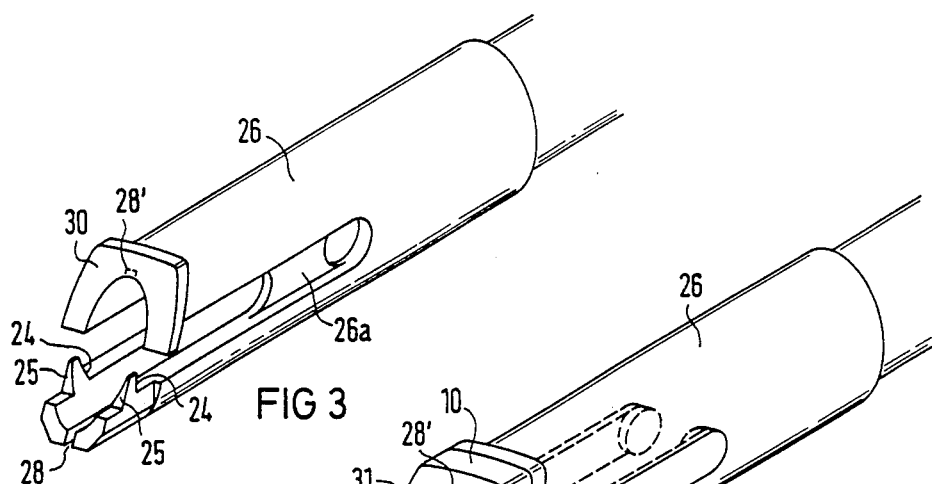
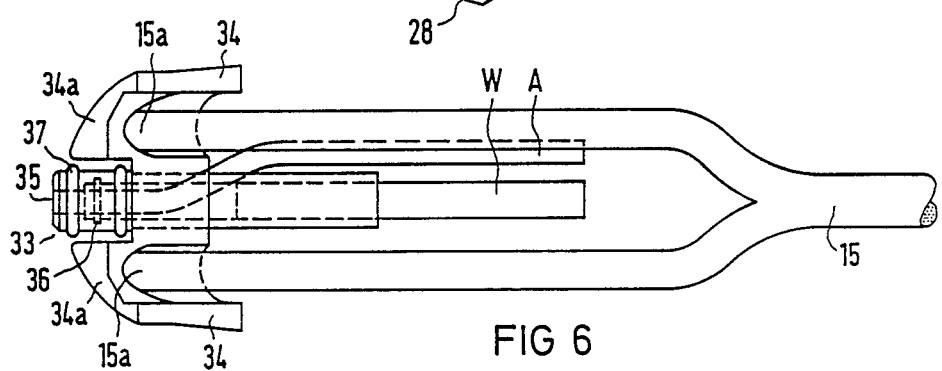
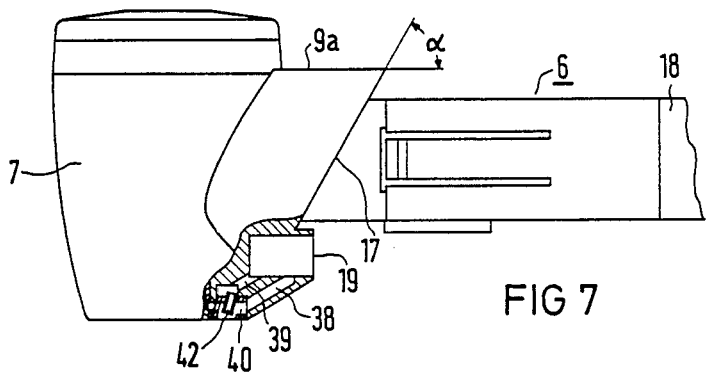

DENTAL HANDPIECE

BACKGROUND OF THE INVENTION

The present invention is directed to a dental handpiece which contains two handpiece parts that are axially connectable to one another by means for latching or a catch mechanism. These handpiece parts each have surfaces at the connection formed by the joint therebetween which reside correspondingly opposite of one another in the connected condition. One of the parts is a gripping part which is connectable to a supply hose and the other part is a head part which is removably held at the free end of the gripping part. The head part contains a head housing for acceptance of a tool and a neck portion extending from the housing and having a guide shank for the acceptance of the drive shaft for the driving of the tool. In addition, the handpiece will have agent lines for water and air and means for conducting light with at least the means for conducting light emerging from the gripping part at the end of the gripping part facing the head part.

A dental handpiece is disclosed in U.S. Pat. No. 4,348,180, whose disclosure is incorporated by reference, and which patent was based on the European application resulting in European Pat. No. 0,029,862. This handpiece has a head part which contains a catch mechanism in the immediate proximity of the head housing. This catch mechanism includes a cylindrical outside sleeve which is deformable by pressing on both sides and has longitudinally extending catch noses on the free end of the sleeve which will engage correspondingly constructed notches or recesses in the gripping part when the head part is plugged onto the gripping part.

The outside sleeve, which serves as an actuation element, takes up a relatively large area in the immediate proximity of the head housing so that it becomes difficult to allow light and under given conditions other agents to emerge, such as at the end of the gripping part, so that the agents can be optimumly utilized at the preparation location. The latter is of particular significance for light because in order to avoid heavy shadows and light losses, one would like to have the light exit end approach as close as possible to the head housing and extend relative steeply there so that the end of the light conduit extends approximately parallel to the tool axis. In order to achieve this in the known handpiece, the light conductor would have to be conducted through the relatively long neck part of the head part and this means an additional connection in the light conductor. Since light transmission losses are associated with each connection of the light conductor, it is desirable to avoid conducting light in the neck part.

SUMMARY OF THE INVENTION

The present invention is directed to providing a dental handpiece having a catch mechanism wherein it is possible to be able to conduct agents, particularly light, as closely as possible to the preparation location while largely avoiding heavy shadows, and unnecessarily relatively involved parting or, respectively, coupling locations which would produce additional losses.

To accomplish these goals, the dental handpiece of the present invention includes a gripping part which is connected to a supply hose and on one end receives a head part which contains a head housing for the acceptance of a tool and a neck part having a guide shank extending therefrom. The one end of the gripping part and the corresponding surface of the head part are obliquely inclined relative to the axis of the guide shank with the surface of the neck part being inclined so that the side adjacent the tool is closest to the tool and the gripping part includes agent lines for air and water and means for conducting light with at least the means for conducting light emerging from the gripping part at the one end adjacent to the obliquely inclined end surface.

The oblique end surfaces between the head part and the gripping part make it possible to conduct the agents extremely close to the head housing and also to create adequate space at the other end or side of the head housing in order, for example, to provide fastening means for the head part shank or as warranted to also be able to arrange the actuation element for the catch mechanism. The oblique surface also facilitates the positioning and alignment of the handpiece parts when they are being interconnected. What is particularly facilitated is the position in conjunction with the guide element, for example, a guide nose or projection which is provided axially and radially projecting at one of the handpiece parts and interacts with the oblique surface of the other handpiece part so that the parts are aligned functionally relative to one another when the parts are joined. The guide element, which advantageously forms an anti-twisting protection at the same time together with the correspondingly fashioned recess in which it is received, can be arranged either on the upper side or surface of the head part or on the underside or surface of the gripping part.

The oblique surfaces can be arranged to be curved surfaces or fashioned to lie in one plane in the aforementioned way. An arrangement at the acute angle of about 60° relative to the axis of the guide shank is advantageous whereby the oblique surface of the head part can be tangential to the head housing or can slightly intersect it. One part of the surface at the gripping part side is advantageously formed by a carrier part in which the lines for agents, such as air and water, as well as the arrangement for projecting light are arranged. These lines are either all discharged with their ends directed towards the tip of the tool; however, it can also be advantageous wherein the light conductor comprises two conduits ends which direct air lights into cheeks arranged on both sides of the carrier part which continue the contour of the neck part and the agents, such as air and water, are conducted into the head housing where they emerge at a lower end face of the head housing in a known way via one or more discharge openings.

Other advantages and developments of the present invention will be readily apparent from the following drawings, description and claims.

BRIEF DESCRIPTION OF THE DRAWINGS

FIG. 1 is a perspective view with portions broken away of a dental handpiece in accordance with the present invention;

FIG. 2 is an enlarged perspective view of a head part of the present invention;

FIG. 3 is an enlarged perspective view of a guide sleeve in accordance with the present invention with portions of the gripping part being removed;

FIG. 4 is an enlarged perspective view of the guide sleeve of FIG. 3 with the actuation elements of the latching mechanism installed;

FIG. 5 is an enlarged perspective view of a carrier part for agent lines which is connectable to the head part of FIG. 2;

FIG. 6 is a plan view of the carrier part of FIG. 5;

FIG. 7 is a side view of the head part with portions broken away; and

FIG. 8 is a partial top plan view with portions broken away illustrating an embodiment of a guide element for the present invention.

DESCRIPTION OF THE PREFERRED EMBODIMENTS

The principles of the present invention are particularly useful when incorporated in a dental handpiece 1 of FIG. 1. The dental handpiece 1 has a drive part 4 which on one end has a connector 2 for connection to a supply hose 3. The supply hose 3 provides various lines for agents, such as water line W, air line A and electrical energy line E, to the handpiece. On the other end of the drive part 4 is a gripping part or grip piece 5, which is connected to a head part 6. The head part 6 contains a head housing 7 which mounts a tool 8 for rotation and also contains a short neck part 9. To disconnect the head part 6 from the grip part 5, actuation elements 10 of a catch mechanism for locking the head part 6 relative to the grip part 5 are provided.

The drive part 4 contains a drive motor 11, which can be either electrically driven or air driven and has a drive shaft with a plurality of drive shaft sections 12 and 13 (FIG. 2) coupled in a standard way for driving the tool 8 which is held in the head housing 7. The drive part 4 further includes a miniature incandescent lamp 14 which, like the motor 11, is supplied with voltage from the energy lines E in the supply hose 3. The light exit location of the lamp 14 resides correspondingly opposite an end of a light conductor 15, which like the lines A for air and W for water are positioned within the drive part 4 and extend into the gripping part 5 in a suitable manner. The light conductor 15 is divided into two sections in the region of the head part with ends 15a of the two sections forming light exit locations on both sides of the head part which exit locations are directed such that an adequately large luminous field is generated in the region of the tip of the tool 8.

As best illustrated in FIG. 2, the neck part 9, which is connected to the head housing 7, has an obliquely inclined surface 17 from which a guide shank 18 extends and has a drive shaft section 13 mounted for rotation. In addition, a shoulder part 20 extends from the surface 17 and has a bore or socket 19. The oblique surface 17, as best illustrated in FIG. 7, is inclined at an angle α of 60° relative to the axis of the shank 18 which axis extends at 90° to the axis of rotation for the tool in the head housing 7. The surface 17 is inclined so that the lower edge is immediately adjacent or emerges with the lower portion of the housing 7. The oblique surface 17 is thereby attached to the neck part at such a distance towards the head housing that it is practically tangential to the head housing at its lower end and an adequate space remains in the upper neck area 9a in order, for example, to be able to accommodate fastening means, such as screws, for the shank 18 or as warranted actuation means for a catch mechanism. In the present examplary embodiment, the actuation element, however, is a component part of the gripping part 5.

The catch mechanism, as illustrated, is composed of an active catch element in the form of a sleeve 22 which is secured in an anti-twist fashion on the shank 18 of the head part 6. The sleeve 22 comprises resilient tabs 23 extending parallel to the axis of the shank. When in a locking condition, the tabs 23 have ends 23a which are seated against stop faces 24 of catch hooks 25 of a guide sleeve 26 (FIG. 3) which is in the gripping part 5. To provide an anti-twist connection between the shank 18 and the sleeve 26, the sleeve 26 contains a longitudinal slot 28 which receives a catch nose or an axially extending key or projection 29.

The actuation element 10, which is shown with the guide sleeve 26 in FIG. 4, serves the purposes of unlocking the latching between the ends 23a and the stop surfaces 24. The actuation element 10 is fashioned in an inverted U-shaped configuration and is placed clamp-like onto the sleeve 26 between the head part and the gripping sleeve and is secured against axial slippage by laterally retaining arms 10a which are received in axially extending guide grooves 26a (FIG. 3) of the sleeve 26. The actuation element 10 is resilient fashioned and by means of laterally pressing as indicated by the arrows in FIG. 4 will urge the tabs 23 and their ends 23a which are pressing resiliently against the stop faces in the locked condition to be pushed radially inward into a recess 27 provided on the shank 18 so that the latch connection is disengaged. The head part can then be axially pulled out of or from the guide sleeve 26 or, respectively, the gripping part 5.

As mentioned, the guide sleeve 26 contains a longitudinal slot 28 for receiving the key 29 which are illustrated as being located on the undersurface of the sleeve and shank. At the end face, the guide sleeve also has an oblique end face 30 corresponding to the surface 17 and the actuation element 10 is pressed against this surface 30. The actuation element itself contains a surface 31 which corresponds with the surface 17 in the coupled condition of the handpiece parts 5 and 6.

It is particularly advantageous to arrange the guide slot and projection or catch nose not on an underside but an upper surface of the head part and gripping part as indicated in FIGS. 2 and 3 by the positions 28' and 29'. When the gripping part with the guide sleeve is slipped onto the head part, a precise positioning, for example an alignment of the parts to be connected to one another which is functionally suited, can thus, be achieved. When the head part and gripping part are twisted relative to one another, they can be put in place but are not aligned functionally relative to each other. In this condition, the oblique face 31 of the actuating element 10 will engage the catch nose or key 29' and slide therealong with relative rotation between the parts until the catch nose or key 29' enters the slot 28'. This same effect can also be achieved when the catch nose or key is arranged on the gripping part and the slot or other recess corresponding to the catch nose is provided on the head part. In this case, however, the parts are then to be arranged preferably on the bottom or undersurface of the head part and the gripping part. The catch nose, as shown, can be a radially projecting catch nose but can also be a pen or peg projecting parallel to the axis. The catch nose can advantageously be combined with the line ends carrying the agent which correspond to the connecting nozzle to be described hereinbelow.

An example of another construction for the key is shown in FIG. 8 and is constructed of laterally resistant spring elements, which extend in a longitudinal direction to be received in the guide grooves, such as 28'. In this embodiment, the head part 6 is illustrated as having the key or guiding projection on an upper surface and is composed of two plate-like spring elements 43 and 44 which are arranged so that they stand on edge with one end of the elements 43 and 44 being received in a recess 45 in the neck part 9. The lower edges of the elements lead into a longitudinal groove in the shank 18. When they are in the connected state, the elements 43 and 44 are received in the longitudinally extending groove, such as 28', of the gripping part 5 or the guide sleeve 26. The work tolerance of the longitudinal groove 28' are balanced by the spring action so that a good fit always exists between the head part and gripping part. Differently shaped spring elements, for example a wavy spring plate, can also be used and positioned on edge. Also, a tubular spring formed by a longitudinally slit sleeve can be provided in place of the two spring plates 43 and 44.

As illustrated in FIG. 1, below the actuation element 10 is a carrier part 32 for the agent lines that are to extend between the gripping part 5 and the head part 6. As illustrated in FIGS. 5 and 6, the carrier part 32 contains a central connecting nozzle 33 and a pair of cheeks 34 projecting therefrom on both sides which cheeks have respective openings for the emergence of the light conductor ends 15a. The cheeks 34 are fashioned so that they both continue the outer contour of the neck part 9 in this particular region and have an end surface or face 34a to press against the oblique surface 17 on opposite sides of the shoulder 20 when the head part is coupled on the grip part to form a detent therebetween. The connecting nozzle 33 is engaged in the socket or bore 19 (FIG. 2) of the head part 6 and conducts the agent, such as air and water, into the lower part of the head housing 7.

It may be seen that the light conductor 15 is divided into two conductor sections whose ends 15a project light on both sides of the cheeks 34. The air line A and the water line W discharge into the connecting nozzle 33 which has a central axial opening on one end and also is provided with a slot opening 36 with spaced sealing rings 37 on the nozzle 33 in axial spacing so as to seal the opening 36 from the opening 35 when the nozzle is inserted in the bore 19. As illustrated, when the connecting nozzle 33 is plugged into the bore 19, one agent, such as air, is conducted into the annular chamber 40 (FIG. 7) by a channel 38 and another agent, such as water, is mixed thereto as it flows through a channel 39 and one or more nozzles 42 which are distributed over the circumference of the annular chamber 40. The mixture of air and water will be discharged through openings 41 (FIG. 2) so that the air/water mixture or spray is directed at the preparation location present opposite the exit openings 41.

The connecting nozzle 33 with the openings 35 and 36 projects somewhat axially beyond the end face 34a of the lateral cheeks 34 of the carrier part 32. This has the advantage that when the head part 6 is not plugged into the gripping part 5 and agents are mistakenly delivered, the agents cannot proceed into the gripping part which contains the drive shaft and their bearings. Thus, the risk of corrosion is reduced or, respectively, largely impossible.

Although various minor modifications may be suggested by those versed in the art, it should be understood that we wish to employ within the scope of the patent granted hereon, all such modifications as reasonably and properly come within the scope of our contribution to the art.

We claim:

1. A dental handpiece including at least two handpiece parts axially connectable to one another and means for latching the two parts in an assembled position, said handpiece parts including a gripping part connected to a supply hose and a head part removably mounted on a free end of the gripping part, said head part containing a head housing for the acceptance of a tool and a short neck part having a mating surface with a guide shank extending therefrom along an axis, said gripping part at a free end having an end surface with an axially extending bore for receiving said guide shank, said parts having agent lines for at least one agent and a light conductor arranged in the handpiece having light emerging from the gripping part at a free end of the gripping part adjacent said end surface, said end surface of the gripping part and the mating surface of the neck part residing correspondingly opposite one another and being obliquely inclined relative to the axis of the guide shank with the direction of inclination being such that the surfaces extend essentially adjacent to a lower end of the head housing.

2. A handpiece according to claim 1, wherein the mating surface and end surface are inclined at an acute angle to the axis of the guide shank, said angle being approximately 60°.

3. A handpiece according to claim 2, wherein each of the surface lies in a plane.

4. A handpiece according to claim 3, wherein the surfaces are tangential with the head housing.

5. A handpiece according to claim 1, wherein the head part and the gripping part have a coacting guide element and recess to form means to prevent twisting between the parts.

6. A handpiece according to claim 5, wherein the guide element is arranged at the end of the gripping part and contains at least one of said agent lines.

7. A handpiece according to claim 6, wherein a surface of the gripping part facing a lower portion of the head housing terminates in a carrier part for said guide element containing the ends of the agent lines.

8. A handpiece according to claim 7, wherein the agent lines discharge into the carrier part with their ends being directed towards the tool tip.

9. A handpiece according to claim 7, wherein the agent lines are for air and water which lines end in the carrier part in a central connected nozzle, said nozzle being received in a channel provided in the head part, said carrier part having lateral cheeks continuing the contour of the neck part of the head part, said lateral cheeks supporting ends of a light conductor with each end directed towards the tool supported in the head housing.

10. A handpiece according to claim 9, wherein the channel of the head housing is provided in a head housing shoulder serving the purpose of anti-twist protection and for centering.

11. A handpiece according to claim 9, wherein the cheeks have end faces arranged on both sides of the connecting nozzle pressing against the mating surface of the head part when the head part is coupled therewith, said end faces of the cheeks forming a detent.

12. A handpiece according to claim 9, wherein the gripping part has a guide sleeve forming said bore and having end faces of the guide sleeve forms a detent.

13. A handpiece according to claim 9, wherein two agent lines are connected to the connecting nozzle, said agent lines discharging at spaced openings on said nozzle with one of said openings being an axial opening sealed from the other by an o-ring when said nozzle is received in a couple condition in the channel of the head part, said channel of said head part being formed in a head housing shoulder and having passages extending from said channel and being in communication with discharge openings arranged on a lower surface of the head housing.

14. A handpiece according to claim 1, wherein the gripping part has a carrier part adjacent a lower portion thereof, said means for latching including an actuation element having a U shape and being mounted on an oblique surface of the gripping part above the carrier part, said actuation element and said carrier part forming the oblique end surface of the gripping part engaging the mating surface of the neck portion.

15. A handpiece according to claim 1, wherein the mating surface of the neck part and the free end surface of the gripping part are planar surfaces extending at an angle of approximately 60° to the axis of said guide shank and the surfaces being tangential to the head housing, said gripping part having a carrier part adjacent a lower edge forming a portion of the free end surface of the gripping part, said carrier part having a connection nozzle projecting axially thereto and received in a socket formed in the neck part of the head part.

16. A handpiece according to claim 1, which includes means for preventing twisting between said parts including a coacting guide member and recess in the parts, said guide member being formed by at least one spring element having spring resistance in a crosswise direction being mounted to be received in a guide groove forming said recess.

17. A handpiece according to claim 16, wherein two spring elements are provided and are mounted to stand on edge in a groove in the head part and have a longitudinal lower surface being received in a guide groove formed in said gripping part.

* * * * *